United States Patent [19]

Masuhara et al.

[11] Patent Number: 5,135,686
[45] Date of Patent: * Aug. 4, 1992

[54] METHOD AND APPARATUS FOR CONTINUOUS HARDENING OF LIGHT-CURING RESINS

[75] Inventors: Eiichi Masuhara, Tokyo; Shigeo Komiya, Urawa; Takeyuki Sawamoto, Tokyo; Shusuke Kimura, Yono; Koji Ozeki, Yono; Kensuke Nakajima, Yono; Kiyomi Sanbonmatsu; Noboru Nishiyama, both of Yono, all of Japan

[73] Assignee: Japan Institute of Advanced Dentistry, Tokyo, Japan

[*] Notice: The portion of the term of this patent subsequent to Aug. 4, 2009 has been disclaimed.

[21] Appl. No.: 459,161

[22] Filed: Dec. 29, 1989

[30] Foreign Application Priority Data

Sep. 1, 1989 [JP] Japan ................. 1-226971

[51] Int. Cl.5 ............................................ B29C 35/08
[52] U.S. Cl. ........................................ 264/22; 264/1.4; 264/17; 264/19; 264/40.6; 264/297.7; 425/143; 425/174.4
[58] Field of Search ............ 264/17, 18, 22, 25, 264/26, 19, 1.4, 40.7, 297.7; 425/143, 174, 174.4, 808, 150

[56] References Cited

U.S. PATENT DOCUMENTS

| | | | |
|---|---|---|---|
| 4,073,835 | 2/1978 | Otsuki et al. | 264/22 |
| 4,132,518 | 1/1979 | Rips | 425/143 |
| 4,267,133 | 5/1981 | Kohmura et al. | 264/22 |
| 4,329,135 | 5/1982 | Beck | 425/174 |
| 4,439,380 | 3/1984 | Michl et al. | 264/22 |
| 4,624,810 | 11/1986 | Sisbarro | 425/174.4 |
| 4,879,073 | 11/1989 | Kromrey | 264/22 |
| 4,890,997 | 1/1990 | Beins et al. | 264/22 |
| 4,913,859 | 4/1990 | Overton et al. | 425/174.4 |

FOREIGN PATENT DOCUMENTS 3428688 2/1986 Fed. Rep. of Germany ... 425/174.4

Primary Examiner—Jeffery Thurlow
Assistant Examiner—Mathieu Vargot
Attorney, Agent, or Firm—Armstrong, Nikaido, Marmelstein, Kubovcik & Murray

[57] ABSTRACT

A method to continuousky harden light-curable resins, by irradiating at least one shaped article made of a light-curable resin by continuously moving the article past a multiplicity of light sources while changing the flux of the irradiated light in multiple steps corresponding to the moving positions of the object and an apparatus to accomplish this method including means to continuously move the article relative to the multiple irradiation sources and means to adjust the flux density in multiple steps corresponding to the moving positions of the article. Specifically, the flux density of the light irradiated on the moving article is changed stepwide depending upon the position and the location of the article and the polymerization speed of the article and the hardening depth can be controlled in relation to its position and time.

18 Claims, 7 Drawing Sheets

METHOD AND APPARATUS FOR CONTINUOUS HARDENING OF LIGHT-CURING RESINS

BACKGROUND OF THE INVENTION

The present invention relates to a method and an apparatus for continuous hardening of light-curing resins, and in particular to a method and an apparatus for continuous hardening of light-curing resins by continuously hardening the objects made of light-curing resins while they are in movement.

The method and the apparatus for hardening the light-curing resins are divided into those using ultraviolet light and those using visible light.

The hardening apparatus using ultraviolet light is mostly used for the hardening of the thinner objects with thickness of several $\mu$m to several hundreds of $\mu$m such as film, ink, coating film, etc. of light-curing resins.

These apparatuses comprise the continuous moving means such as belt conveyor, and the object thinly coated with light-curing resins are continuously hardened by irradiating ultraviolet light. The apparatuses have high productivity and are widely used.

On the other hand, the method and the apparatus using visible light are applied, for example, for the hardening of dental laboratory products using composite resin in the field of dentistry. For example, the Japanese Provisional Patent Publication Sho 62-38149 describes an irradiation apparatus having fluorescent lamp to emit the visible ray of 400-500 nm, and the Japanese Provisional Patent Publication Sho 62-47354 discloses an irradiation apparatus to irradiate the light from halogen lamps on the objects on a turn-table.

The hardening apparatus as described above is designed in batch type, which normally hardens one or more objects at one time.

However, when ultraviolet light is used as described above, high productivity is obtained, whereas the object cannot be hardened to its deep core. In case of dental material with thickness of 1 mm or more, the interior of the object often remains unhardened, and the hardness and the mechanical strength of the products are reduced.

To solve these problems, photopolymerization type resin is coated thinly, and ultraviolet light is irradiated for hardening. Then the light-curing resins is thinly applied again, and ultraviolet light is irradiated again for hardening, repeating the procedure by many times. This requires a complicated procedure and much time.

Because a normal ultraviolet light irradiation apparatus has constant radiation flux density, the rate of polymerization cannot be controlled. If the radiation flux density is increased in order to harden thick light-curing resins, the objects are rapidly polymerized and hardened, and internal distortion occurs inside the hardened object during polymerization, and this results in the decrease of mechanical strength or the reduction in dimensional accuracy. On the other hand, by the hardening apparatus using visible light, it is possible to harden easily the object with thickness of 1 mm or more, whereas only the conventional batch type apparatus is available, and the productivity is low.

Further, the illuminance is fixed in the conventional type visible light hardening apparatus. If the illuminance is increased to achieve the hardening to the deep core of the object, the rate of polymerization cannot be controlled as in case of ultraviolet light. As the result, internal distortion occurs inside the hardened object during polymerization, and this results in the decline of mechanical strength and lower dimensional accuracy.

Also, in the apparatus using ultraviolet light or visible light, when the flux density of the irradiation is weak, light energy converted to heat is low. Thus, the atmosphere temperature is not increased sufficiently, and this leads to lower hardness and poor mechanical strength of the hardened object. On the other hand, if the flux density of the irradiation light is strong, the energy to be converted to heat also increases. As the result, the hardened object is heated more than actually required, causing thermal expansion. This results in the lower dimensional accuracy of the products when the hardening is completed.

SUMMARY OF THE INVENTION

To solve these problems, the present invention offers (1) a method for continuous hardening of light-curing resins, characterized in that the flux density of the irradiation light is changed in multiple stages corresponding to the positions of the objects when the light is irradiated on the object made of light-curing resins continuously in movement, and (2) an apparatus for continuous hardening of light-curing resins, comprising an equipment for continuously moving the objects and an irradiation light regulating equipment, characterized in that the irradiation light regulating equipment contains a light source and a means to adjust and irradiate the irradiation light by changing the flux density in multiple steps according to the positions of the objects to be irradiated.

Namely, the flux density of the irradiation light on the objects in movement is changed stepwise according to the position and the location of the objects to be irradiated.

Thus, the flux density of the irradiation light irradiated on the objects is changed according to the movement of the object. As the result, the polymerization speed and the depth of the hardening of the object can be controlled in relation to the position and the time.

The "continuous movement" as described in this invention is defined as the status, in which the objects are introduced into the hardening apparatus one after another and are carried out of there. Accordingly, this includes not only the case where the object is moved smoothly at all times but also the case where it is moved intermittently.

The time from the introduction of the objects into the hardening apparatus to the moving out is preferably within the range of 1 second to 24 hours, and more preferably within the range of 10 seconds to 3 hours.

The moving mechanism may include the means to move the objects continuously at all times such as belt conveyor or turntable, or the moving means to move the objects stepwise according to the stroke such as walking beam conveyor, pneumatic or hydraulic cylinder, etc. Or, pulse motor may be used, which moves the objects by numerical control.

The movement of the irradiated objects may be linear or rotary movement on the same plane or upward or downward movement.

As the light source to generate irradiation light, the light source used for normal photopolymerization such as halogen lamp, xenon lamp, fluorescent lamp, high-pressure mercury lamp, low-pressure mercury lamp, arc discharge lamp, etc. may be used.

The light source may be furnished with a reflection mirror or a diffusion plate as already known or with a heat-cut filter to provide the distribution of the flux density as desired or to give the effect to reduce the temperature rise of the irradiated objects.

According to the present invention, the irradiation light with flux density changing in multiple stage is irradiated on the objects, which are moved continuously. Here, the wording "flux density changing in multiple stages" means that the flux density of the irradiation light received by the object to be irradiated when it is introduced into the equipment by a moving mechanism significantly varies during the process of moving from one position to another in the apparatus. (For example, 100 kiloluxes at the point A, and 200 or 10 kiloluxes at the point B.)

Here, it is preferable to change the flux density of irradiation light within the range of 0.01 to 1000 milliwatts/cm$^2$ in case the irradiation light is ultraviolet light, and more preferably in the range of 0.1–100 milliwatts. In case the irradiation light is visible light, the flux density of the irradiation light is preferably changed in the range of 100 luxes to 10,000 kiloluxes, and more preferably in the range of 1,000 luxes to 1,000 kiloluxes.

In general, the flux density of the irradiation light is inversely proportional to the square of the distance between the light source and the object, whereas the relation between the position of the object in the hardening apparatus and the flux density of the irradiation light in the present invention differs from it. In graphic representation, the relation can be expressed by an exponential curve, an inclined straight line or a step-like figure.

The ratio of the minimum flux density and the maximum flux density of the irradiation light when it is changed in multiple stages is preferably 1:2 or more, and more preferably 1:10 or more.

The flux density of the light irradiated on the object may be continuously or discretely changed. For example, in the early stage of polymerization (near the inlet of the apparatus), the light of low flux density is irradiated, and the light of higher flux density is irradiated in later stage (near the outlet of the equipment) to hinder the rapid polymerization contraction of the object and to obtain the high-precision polymerized object within short time.

Next, description will be given on the means to change the flux density of the irradiation light on the object in multiple steps (substantially in two or more steps).
(1) The method to provide two lamps with different output power as given in FIG. 1.
(2) The method to provide fluorescent lamp and halogen lamp as given in FIG. 2.
(3) The method to change partially the number of lamps as given in FIG. 3.
(4) The method to provide partially the filter with different light transmittance as given in FIG. 4.
(5) The method to adjust the flux density of the irradiation light of two or more light sources by variable transformer as shown in FIG. 5.

As described above, the flux density of the irradiation light at each position is changed according to the photopolymerization property of the object to be irradiated because the rate of polymerization of the light-curing resins depends upon the flux density of light.

For the object with thickness of 1 mm or more or for light-curing resins filled with filler, visible light from halogen lamp, xenon lamp and fluorescent lamp are suitable.

According to the present invention, it is possible to conceive an apparatus, in which the ambient temperature inside the apparatus can be controlled independently from the flux density of the irradiation light. The control can be performed by providing fan, cooling water, cooler, heater or infrared generator at the desired position in the apparatus. (See FIG. 6.) Further, it is also possible to control the temperature by providing halogen lamp (high temperature range) or fluorescent lamp (low temperature range), considering the types of lamp and the flux density of the irradiation light.

By adopting the method and the apparatus to continuously harden the light-curing resins by this invention, it is possible to produce coating film, paint film, dental laboratory products (artificial tooth, artificial crown, denture base, etc.), light-curing resins mold products by light transmission type mold, etc. at high efficiency and accuracy.

As actual examples of the products using light transmission type mold, there are contact lens, eyeglass lens, microlens, orthodontic bracket, gears, etc.

In addition, the method by this invention is suitable for the sealing of semiconductor device and coating of optical fiber, the bonding of optical components such as prisms, lenses, etc. and the hardening of embedded products by light-curing resins.

According to the present invention, it is possible to obtain the resin hardened products, in which: 1) Defects such as cracks, flaws, internal distortion, etc. occur very rarely during molding when the relatively thick resin molding products are hardened; 2) the molding work can be done easily and continuous production is achievable; 3) the hardened resin products with stable quality can be produced, and 4) the hardened resin products with high dimensional accuracy can be obtained.

DESCRIPTION OF THE PREFERRED EMBODIMENT

In the following, the invention will be described in detail by the embodiments in connection with the drawings.

Embodiment 1

Figure 1:
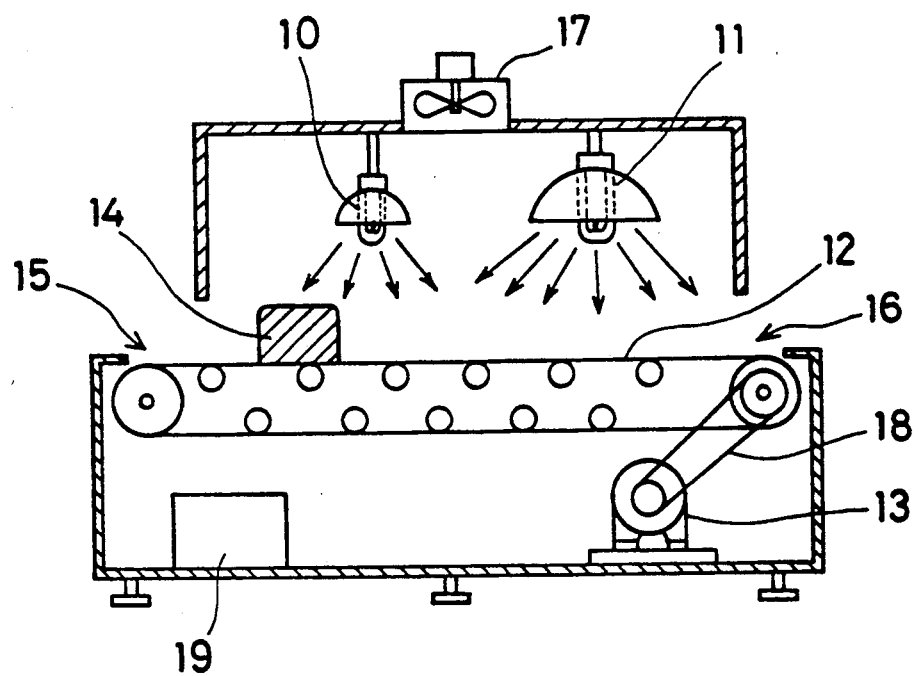
FIG. 1 is a schematical view of the Embodiment 1 of this invention.

FIG. 1 is a schematical view of an apparatus to show the Embodiment 1 of this invention.

In this apparatus, a halogen lamp (10) of small output power (50W) is provided near the inlet (15) of the object to be irradiated and a halogen lamp (11) of large output power (250W) is furnished near the outlet (16).

The flux density of the irradiation light of this apparatus was 12 kiloluxes below the small output halogen lamp (10) and 1,500 kiloluxes below the large output halogen lamp (11).

The mechanism to move the object (14) in the equipment is a conveyor (12) driven by a motor (13) and chain (18).

In the embodiment, the object (14) introduced from the inlet (15) into the apparatus is irradiated with visible light of relatively low radiation intensity by small output halogen lamp (10). When the object (14) is moved toward the outlet 16) as the conveyor (12) is driven, the irradiation light with relatively higher radiation intensity is irradiated on it by large output halogen lamp (11). Thus, the object irradiated with sufficient radiation intensity of light by the large output halogen lamp (11) is brought out of the apparatus through the outlet (16) by the action of the conveyor (12).

The conveyor of this apparatus is 60 cm long, and the halogen lamps (10) and (11) are furnished at 20 cm from the inlet (15) and the outlet (16) respectively.

Next, description will be given on the method to harden the light-curing resins by the apparatus of this embodiment.

First, light-curing resins were prepared by mixing 80 weight parts of bisphenol-A-glycerol modified dimethacrylate, 10 weight parts of methylmethacrylate, 10 weight parts of triethyleneglycol-dimethacrylate, 0.05 weight part of camphorquinone, and 0.05 weight part of N,N-dimethyl-p-toluidine.

Then, a tooth specimen was placed in a polyethylene cylindrical container of 25 mm in inner diameter, 25 mm deep and 2 mm thick. Then, light-curing resins were gently poured into the container without mixing air bubbles until the container is filled up.

The object to be irradiated thus prepared was placed at the inlet (15) of the apparatus and was sent into the apparatus by driving the conveyor (12). The object was moved by the action of the conveyor (12) and was brought out of the outlet (16) The moving speed of the conveyor was 2 cm/min.

When the polymerized object was taken out from hard and transparent resin without cracks and detachment was obtained.

When a number of specimen teeth were embedded by the above method and micro-Brinell hardness of the resin-embedded tooth was determined, it was 21±1 Hb. The products had uniform surface hardness with very few variations.

Embodiment 2

Figure 2:
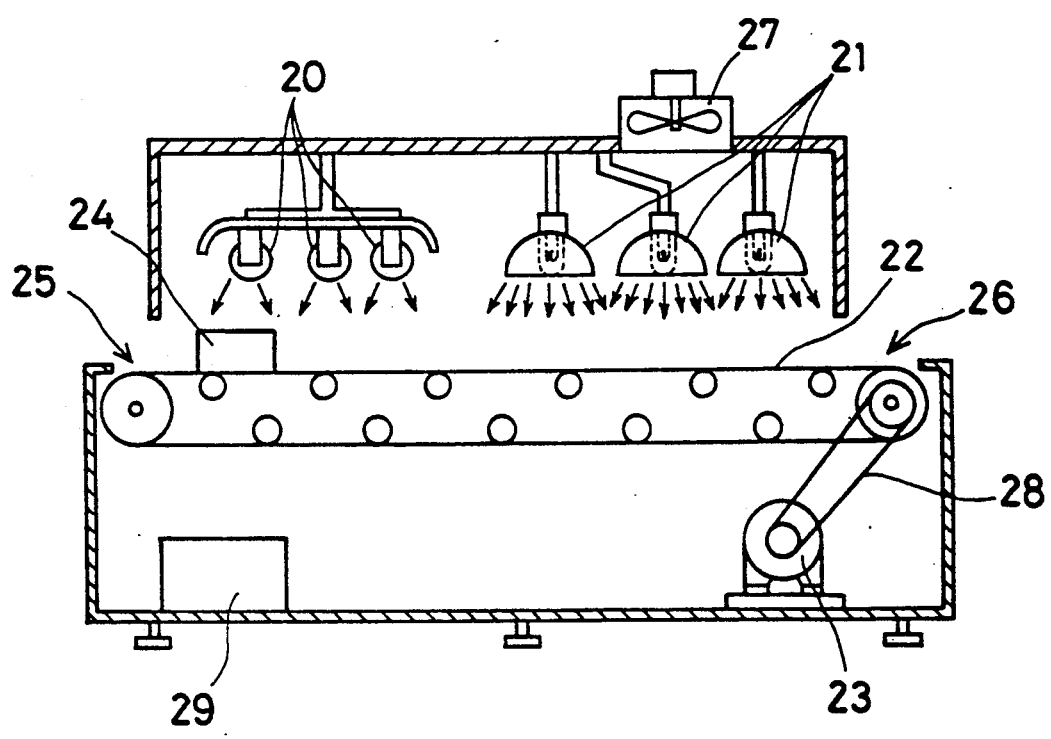
FIG. 2 is a schematical view of the Embodiment 2.

FIG. 2 is a schematical view of the Embodiment 2 by this invention.

The apparatus is provided with three 20W fluorescent lamps (20) and three 250W halogen lamps (21) as the light sources of the irradiation light. As the moving mechanism of the object (24), a conveyor (22) driven by chain (28), transmitting the rotary movement of the motor (23), was furnished similarly to the Embodiment 1.

The object (24) introduced from the inlet (25) into the apparatus is irradiated by the irradiation light of relatively weak radiation intensity by the fluorescent lamps (20). As the object is moved toward the halogen lamps (21) by the action of the conveyor (22), it is irradiated by strong irradiation light of the halogen lamps (21) and is brought out of the apparatus.

The flux density of the irradiation light in this apparatus was 50 kiloluxes below the fluorescent lamps (20), and 1,500 kiloluxes below the halogen lamps (21).

Next, description will be given on the method to harden the light-curing resins by this apparatus.

First, light-curing resins were prepared by maxing 90 weight parts of methylmethacrylate, 10 weight parts of triethyleneglycol-dimethacrylate, 0.1 weight part of camphorquinone and 0.1 weight part of benzoyl peroxide. After stirring thoroughly, they were filled into a light transmission type forming mold for the molding of contact lens made of poly-4-methyl-1-pentene, and it was placed at the inlet (25) of the apparatus.

The moving speed of the conveyor (22) was 5 cm/min., and the conveyor was 100 cm long. When 20 minutes have elapsed after the object was introduced into the equipment by the action of the conveyor (22), the forming mold irradiated by visible light from the fluorescent lamps (2) and halogen lamps (21) was brought out of the outlet (26).

By disassembling this forming mold, the hardened product in shape of contact lens, polymerized by visible light, was obtained. There was neither cracks nor optical distortion in the contact lens product thus obtained, and the radius of curvature was exactly the same as that of the forming mold.

Then, the forming mold with different radius of curvature was prepared and various types of contact lenses having the refraction power in the range from +12 diopters to −16 diopters were produced. In all cases, perfect mold products were obtained.

Embodiment 3

Figure 3:
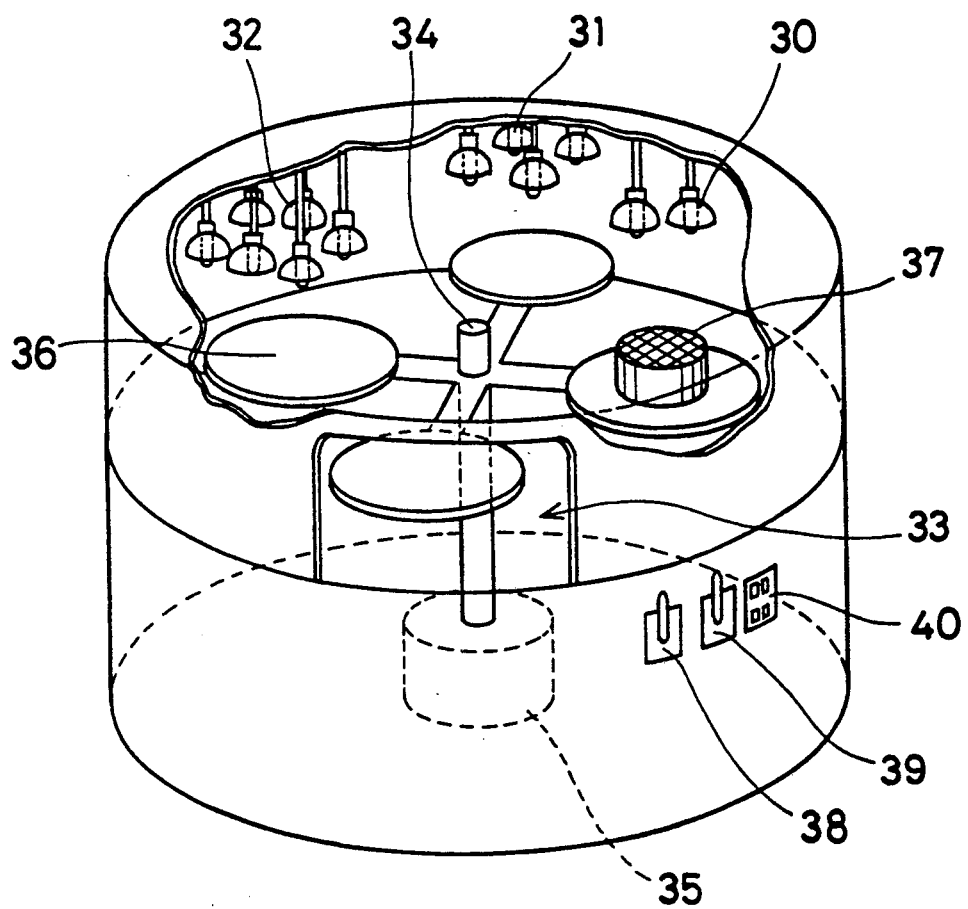
FIG. 3 is a schematical view of the Embodiment 3.

FIG. 3 is a schematical view of the apparatus showing Embodiment 3 of this invention.

In this apparatus, the mechanism to move the object (37) consists of four rotary tables (36), which are rotated by 90 degrees each by the action of a motor (35) after the time set by the timer for rotary table rotation (40) has elapsed. As the light source of this apparatus, 150W halogen lamps are furnished in the quantity of two (30), four (31) and six (32) above three positions of the rotary table. At the positions where halogen lamps are not furnished, the inlet-outlet (33) is provided in order to place the objects into the apparatus or to take them cut of the apparatus when the irradiation is completed.

The flux density of the irradiation light in this apparatus was 180 kiloluxes below the halogen lamps (30), 300 kiloluxes below the halogen lamps (31) and 500 kiloluxes below the halogen lamp (32).

To use this apparatus, power switch (38) is turned on to light up the halogen lamps (30), (31) and (32), and the objects (37) are placed on the rotary tables at the inlet-outlet (33).

After the time to rotate the rotary table (36) is set by the timer (40) for the rotation of rotary table, the switch (39) for rotating the rotary table is turned on to rotate the rotary table (36) by 90 degrees and to move the object to the position where two halogen lamps (30) are lighted.

When the time set by the timer (40) for the rotation of rotary table has elapsed again, the rotary table (36) is rotated again by 90 degrees, and the object is moved to the position where four halogen lamps (31) are lighted. In this way, after the irradiation light from 6 halogen lamps (32) are irradiated on the object, the object (37) comes again to the position of the inlet-outlet (33) Then, the object is taken out of the equipment.

In this apparatus, the inlet and the outlet for the objects are furnished at the same position. For this reason, the operator can set and take out the objects without moving and the space requirement for the apparatus can be minimized.

Next, description will be given on the base where this apparatus is used to produce the resin-embedded product.

After power switch (38) was turned on and the halogen lamps (30), (31) and (32) were lighted up, a stainless steel screw was placed in a cylindrical container similar to the container used in embodiment 1. Light-curing resins were prepared by mixing 68 weight parts of bisphenol-A-glycerol modified dimethacrylate, 15 weight parts of methylmethacrylate, 7 weight parts of laurylacrylate, 10 weight parts of triethyleneglycol-dimethacrylate, 0.05 weight part of camphorquinone, 0.02 weight part of dibenzoyl peroxide and 0.02 weight part of hydroquinonemonomethylether. After this resin was injected into the container, the cylindrical container was placed at the inlet-outlet (33) of this apparatus.

Then, the timer (40) for the rotation of rotary table was set to 10 minutes, and the switch (39) to rotate the rotary table was turned on to operate the apparatus. After 30 minutes, the irradiated specimen came to the inlet-outlet (33) again, and this was taken out and observed. No detachment was observed between the stainless steel screw and the hardened light-curing resin, and the stainless steel screw embedded in hard transparent resin without internal distortion and crack was obtained.

When a number of stainless steel screws were embedded by the above procedure and micro-Brinell hardness of the resin-embedded products was measured, it was 13±1 Hb, and the products showed uniform surface hardness with very few variations.

Embodiment 4

Figure 4:
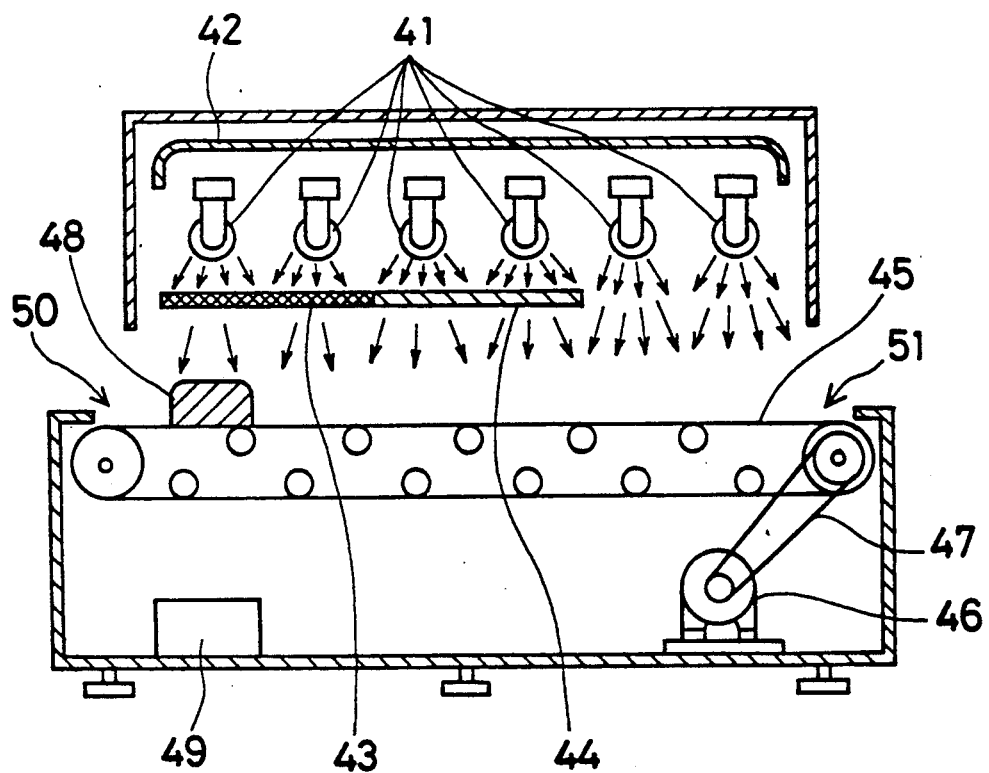
FIG. 4 is a schematical view of the Embodiment 4.

FIG. 4 is a schematical view of the apparatus showing the Embodiment 4 of this invention.

In this embodiment, six 500W high-pressure mercury lamps (41) furnished with reflection plate (42) are provided as the light sources of t[e irradiation light. A conveyor (45) similar to the one used in the Embodiments 2-3 is employed as the mechanism to move the object (48).

The flux density of the irradiation light is adjusted by two types of light-reducing filters (43) and (44). The light transmittance of the light-reducing filter (43) closer to the inlet (50) is 2%, while that of the light-reducing filter (44) at the center of the apparatus is 50%.

The flux density of the irradiation light in this apparatus is 0.5 milliwatt/cm$^2$ below the light-reducing filter (43), 12.5 milliwatts/cm$^2$ under the light-reducing filter (44), and 25 milliwatts/cm$^2$ where there is no filter.

The light-reducing filters (43) and (44) can be replaced by the one having adequate transmittance depending upon the hardening property of the light-curing resins. By selecting the light transmittance of the light-reducing filters (43) and (44), this apparatus can be applied for the hardening of light-curing resins with different properties.

Next, description will be given to the case where this apparatus was applied for the manufacture of eyeglass lenses.

First, the hard glass molds having concave and convex surfaces of meniscus lenses for eyeglasses were placed face-to-face with each other with a gasket of ethylene-ethylacrylate copolymer inserted between them. By holding the periphery of the mold with a clip, a cavity to form an eyeglass lens was prepared.

Next, light-curing resins were prepared by mixing 50 weight parts of methylmethacrylate, 50 weight parts of KAYARAD DPCA 120 (manufactured by Nippon Kayaku; 6-functional acrylate), and 3 weight parts of 1-hydroxycyclohexyl-phenylketone. After stirring up thoroughly, the resins were injected into the cavity without mixing air bubbles, and this was placed on the inlet (50) of the apparatus.

The conveyor (45) of this apparatus was 200 cm long, and the moving speed of the conveyor was 10 cm/min.

After 20 minutes, the irradiated object was brought out of the outlet (51). When the mold was disassembled and the hardened product was taken out, there was neither crack nor optical distortion, and the eyeglass lens made of hardened light-curing resins having excellent surface hardness was obtained. The optical surface of the eyeglass lens thus obtained was extremely smooth, and the surface accuracy was exactly the same as that of the glass mold.

Also, bi-focal eyeglass lens was produced by this apparatus, using a glass mold having a concaved portion with partial linear steps to produce bi-focal lens. In the eyeglass lens made of hardened light-curing resins thus obtained, no crack was seen at the stepped portion of the lens, and the performance characteristics were as superb as the above eyeglass lens.

When a number of eyeglass lenses made of hardened light-curing resins were produced by this apparatus, the hardened products thus obtained showed very few variations in quality and the productivity was extremely stable.

Embodiment 5

Figure 5:
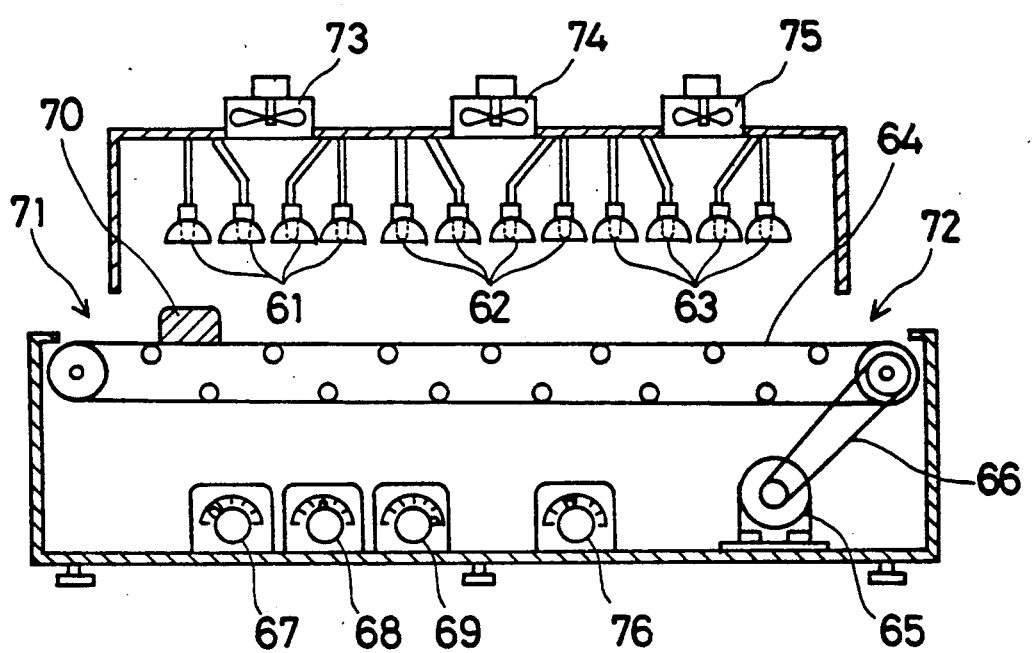
FIG. 5 is a schematical view of the Embodiment 5.

FIG. 5 is a schematical view of the apparatus showing the Embodiment 5 of this invention.

This apparatus is provided with 12 halogen lamps (61), (62) and (63) forming Zone 1 to Zone 3 each containing 4 lamps, above the conveyor (64) as the light sources. The radiation intensity from the halogen lamps (150W×4) in each zone can be adjusted independently by variable transformers (67), (68) and (69) for light adjustment. Also, this apparatus is provided with a variable transformer (76) for conveyor speed adjustment to adjust the rotating speed of the motor (65) and to set the moving speed of the conveyor (64).

Because the flux density of the irradiation light on the object (70) and the irradiation time can be adjusted as desired in this apparatus, the light irradiation condition can be set in wide range depending upon the hardening property of the objects to be irradiated.

Next, description will be given on the case where the orthodontic bracket made of hardened light-curing resins was produced by this apparatus. First, light-curing resins were prepared by mixing 39 weight parts of methylmethacrylate, 52 weight parts of bisphenol-A-ethyleneglycol modified dimethacrylate, 9 weight parts of the hydrophobic silica fume (Nippon Aerosil; R-972), 0.7 weight part of camphorquinone, and 0.7 weight part of benzoyl peroxide. After stirring well, the resins were injected into the light transmission type forming mold for the molding of the bracket made of poly-4-methyl-1-pentene.

Next, the forming mold was placed at the inlet (71) of this apparatus, and the conveyor (6,) was driven for light irradiation.

The conveyor (64) of this apparatus was 180 cm long, and the moving speed was set to 9 cm/min.

The variable transformer (67) for light adjustment of halogen lamps in Zone 1 was set to 30V, the variable transformer (68) in Zone 2 to 78V, and the variable transformer (69) in Zone 3 to 85V.

In tis case, the flux density of the irradiation light was 4 kiloluxes in Zone 1, 140 kiloluxes in Zone 2, and 200 kiloluxes in Zone 3.

After 20 minutes, the light irradiation was completed and the forming mold was sent to the outlet (72). When the forming mold was disassembled and the hardened product was taken out, there was no internal crack. The rough contact surface of the hardened product, caused by the detachment of the contact surface from the inner wall of the forming mold during photopolymerization, was found very rarely. Thus, the bracket made of hard and superb composite resin was obtained.

When a number of orthodontic brackets made of light-curing resins were produced by this equipment, the brackets thus produced showed very few variations in quality, and the production yield was very high.

Specifically, when the base surface of the bracket thus obtained was commented on the holder of the tensile test and piano wire was attached to the wing to measure the tensile strength of the wing by Instron universal tester, the rupture strength was 3.7±0.5 kgf. There were very few variations, and the production yield was more than 90%.

Embodiment 6

Figure 6:
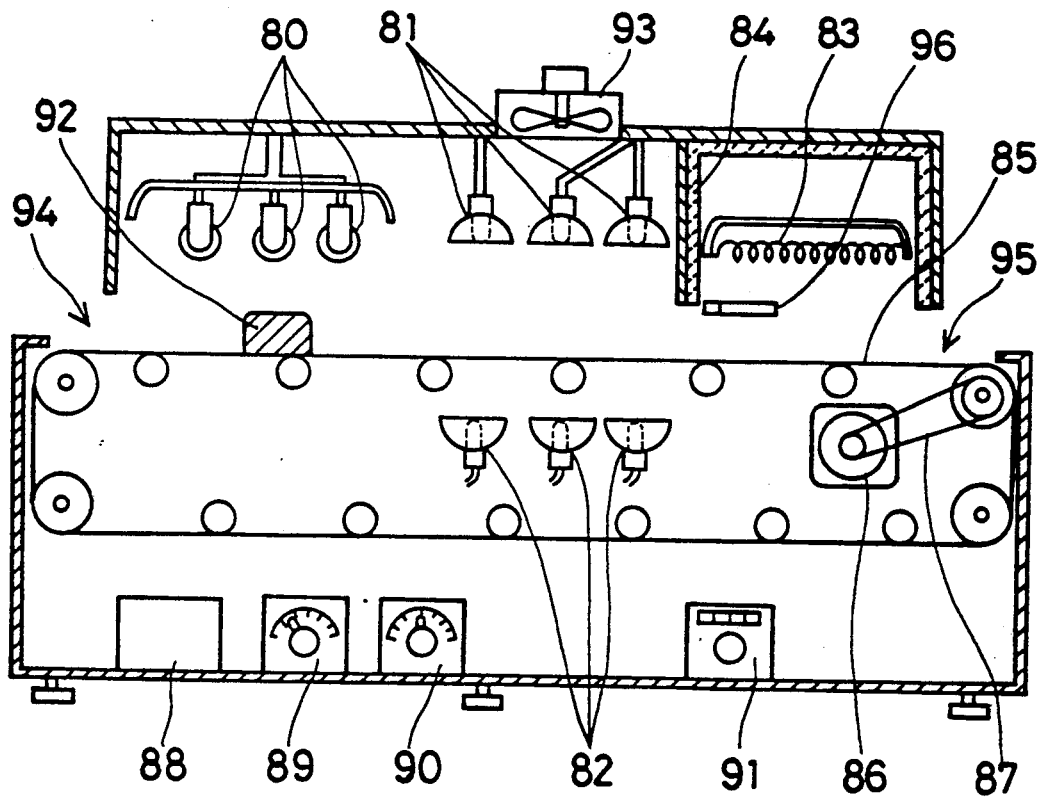
FIG. 6 is a schematical view of the Embodiment 6.

FIG. 6 is a schematical view of the apparatus showing the Embodiment 6 of this invention.

This apparatus is provided with 3 fluorescent lamps (80) giving relatively low flux density and 6 halogen lamps (81) and (82) above and below giving relatively high flux density. Further, it is furnished with a far infrared heater (83) at the outlet (95) of the conveyor (85) to heat the object (92) already irradiated.

Also, of 6 halogen lamps (81) and (82) used in this apparatus, the radiation intensity of 3 lamps above and 3 lamps below are independently controlled by the variable transformers (89) and (90) for the adjustment of halogen lamp light.

In addition, the apparatus is provided with a temperature sensor (96) and a heater temperature regulator (91) to arbitrarily control the temperature of the atmosphere heated by the far infrared heater (83). Accordingly, the flux density of the irradiation light can be set to 2 steps and the object already irradiated can be heat-treated at the desired temperature. Thus, it is possible by this apparatus to perform adequate light irradiation and the heat treatment to improve dynamic and optical properties of the object on a single conveyor.

Because 3 halogen lamps (82) are furnished at lower center of the conveyor (85), the object (92) can be irradiated from above and below, the apparatus is suitable for the hardening of such object, which is too thick to be uniformly hardened on upper and lower surfaces by the irradiation only from one direction or which cannot be irradiated perfectly by the light irradiation from above only.

The conveyor (85) used in this apparatus is designed in the shape of caterpillar, consisting of steel frame attached on Pyrex glass for the convenient irradiation from below by the halogen lamps (82).

Next, description will be given on the case where light-curing resins are hardened by the apparatus of this invention.

The light-curing resins having the same composition as that of the Embodiment 5 were injected into the forming mold made of poly-4-methyl-1-pentene in order to mold the orthodontic bracket, and this was placed at the inlet (94) of this apparatus. The conveyor of this apparatus was 150 cm long, and the moving speed of the conveyor was 5 cm/min.

The variable transformer (89) to adjust the light from upper halogen lamp at the center of the equipment was set to 78V, and the variable transformed (90) to adjust the light from lower halogen lamp was set to 35V. Further, the temperature of the heated atmosphere by the far infrared heater (83) was set to 100° C. by the heater temperature regulator (91).

The flux density of the irradiation light in this apparatus was 45 kiloluxes below the fluorescent lamp (80), 140 kiloluxes below halogen lamps (81), and 6 kiloluxes above the halogen lamps (82).

When 30 minutes have elapsed after the starting of the apparatus operation, the forming mole already irradiated and heat-treated was brought out of the outlet (95). When the mold was disassembled and the hardened object was taken out, a bracket made of composite resin was obtained, which has no crack inside and very few surface roughness. When the base surface of the composite resin bracket was attached on the holder for tensile test and piano wire was bound on the wing to measure the rupture strength of the wing by Instron universal tester, the rupture strength was 5.6±0.5 kgf. This strength was 1.5 times as high as the rupture strength of the bracket obtained in the Embodiment 5.

When a number of orthodontic brackets were molded by this apparatus, the production yield was more than 90% and excellent suitability for mass production was confirmed.

Comparative example 1

In the apparatus as used in the Embodiment 1, the halogen lamp of higher output power (250W) was installed instead of the halogen lamp (10) of lower output power (50W), and tooth embedded sample was produced by the same procedure as in Embodiment 1. The embedded product thus produced showed extreme detachment between the embedded tooth and the hardened resin, and innumerable cracks were found on the surface of the embedded tooth because of abnormal temperature rise exceeding 150° C. during polymerization.

Comparative example 2

In the apparatus used in the Embodiment 2, the halogen lamps (21) were removed and three 20W fluorescent lamps were installed. Then, contact lens was molded by the same procedure as in the Embodiment 2. The molded products thus obtained had neither crack nor optical distortion, and the radius of curvature was exactly the same as that of the forming mold. However, the surface hardness was extremely low, and innumerable flaws occurred on the surface during normal handling, resulting in the loss of transparency and showing the lack of practical applicability.

The fluorescent lamps (20) were removed instead of removing halogen lamps (21) in the Embodiment 2 and three 250W halogen lamps were installed. Then, contact lens was molded by the same procedure as in the Embodiment 2. The molded product thus obtained showed numerable cracks. In many cases, the product had optical distortion inside the lens although it was externally satisfactory, and the produce lacked the suitability for practical production.

Comparative example 3

In the apparatus used in the Embodiment 4, the light-reducing filters (43) and (44) were removed, and the eyeglass lens was hardened by the same procedure as in the Embodiment 4. The hardened object thus produced showed optical distortion when it was thick. When glass mold were taken away, corrugated defects were found on the surface or the surface was deformed.

When the bi-focal eyeglass lens was produced by the same procedure as in the Embodiment 4 by this apparatus, conspicuous crack appeared at the stepped portion of the lens and this was found as not suitable for practical use.

The eyeglass lens made of light-curing resins was molded by the method of the Embodiment 4 using the apparatus of this invention. In the lens with high thickness and larger refraction power, optical distortion and uneven hardening were found.

Comparative example 4

In the apparatus similar to the Embodiment 5, the voltage of the variable transformers (67), (68) and (69) for the adjustment of halogen lamp light from Zone 1 to Zone 3 was set to 85V, and the composite resin bracket was hardened by the same procedure as in the Embodiment 5. The bracket thus produced showed cracks at the slot in many cases. The production yield was less than 70%, showing low productivity.

Comparative example 5

Figure 7:
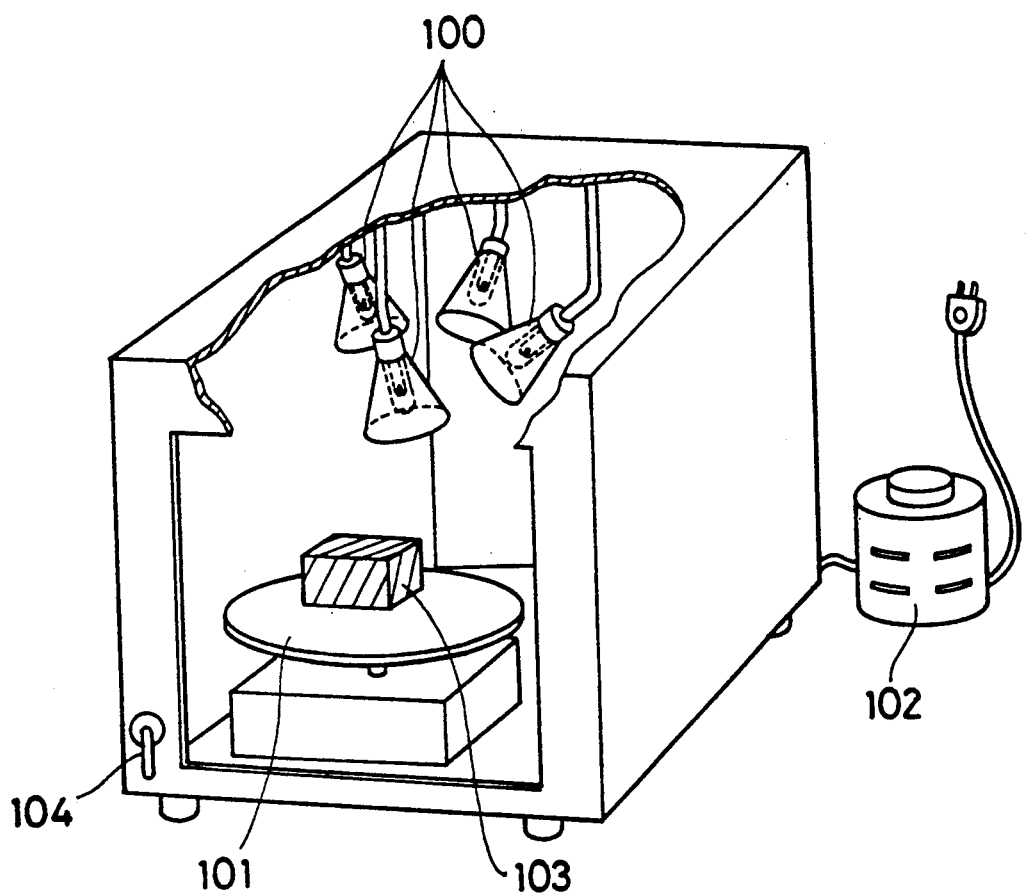
FIG. 7 is a schematical view of a comparative example.

As shown in FIG. 7, four 150W halogen lamps (100) were installed above a turntable (101) with the object (103) to surround it. For this batch type hardening apparatus, a variable transformer (102) for the adjustment of light was provided.

After light-curing resins were injected into the light transmission type mold for the bracket by the same procedure as in the Embodiment 5, the object was hardened by the following procedure: The voltage of the variable transformer (102) for light adjustment was set to 30V, and the light was irradiated for 10 minutes on the object (103). Then, the voltage of the variable transformer (102) for light adjustment was set to 78V, and light was irradiated for 10 minutes. Finally, the voltage was set to 85V, and light was irradiated for 10 minutes.

When a number of brackets were produced by repeating the above procedure, the molded composite resin brackets showed no defect such as internal crack or surface roughness, whereas there were variations in the rupture strength of the wing, and the quality was not stable.

Also, the molding procedure was complicated, and the productivity was low.

As described for the above embodiments, the method and the apparatus for the continuous hardening of light-curing resins according to the present invention have the following features: 1) The defects such as crack, flaws, internal distortion, etc. rarely occur even when the relatively thick resin object is hardened; 2) Resin molding can be done in easy and simple manner, and continuous production is achievable; 3) The hardened resin products obtained have stable quality; 4) The hardened resin products with high dimensional accuracy are obtained.

What we claim is:

1. A method to continuously harden at least one molded shaped article, comprising a resin containing composition which is visible light curable, which comprises: providing, in an enclosed space, a multiplicity of groups of aligned sources of visible light; moving said article and said visible light source groups relative to each other in relative respective alignment; continuously exposing said article to the radiation of all of the visible light sources along its path of relative movement; independently controlling said groups of visible light sources to emit different luminous flux densities from different of said groups corresponding to the position of said article relative to said visible light source; continuously irradiating said article with said visible light to the extent of about 100 to 1,000,000 luxes sufficient to visible light cure and harden said resin; providing sensing means to detect the temperature proximate to said shaped article; independently controlling the temperature of the environment about said shaped article, responsive to said sensing, during said irradiation, whereby said environment temperature is controlled to a predetermined value independent of said radiation and independent of the curing of said resin; and thus producing a cured hardened resinous article.

2. A method as claimed in claim 1 wherein a multiplicity of resinous articles is continuously cured.

3. A method as claimed in claim 1 wherein at least some of said groups of visible light sources comprise a single visible light source.

4. A method as claimed in claim 1 wherein said temperature is controlled by cooling.

5. A method as claimed in claim 1 wherein said temperature is controlled by heating.

6. A method as claimed in claim 1 wherein said groups of visible light sources are linearly aligned, and said article moves linearly in alignment therewith.

7. A method as claimed in claim 1 including controlling the temperature to about 20 to 95° C.

8. A method as claimed in claim 1 wherein said luminous flux density changes are step-wise.

9. A method as claimed in claim 1 wherein said luminous flux density changes are coordinated with a predetermined schedule of the depth of said hardening in relation to the time of curing.

10. An apparatus adapted to visible light cure and harden at least one molded shaped article, comprising a resinous composition which is curable by exposure to visible light, which comprises: an enclosure containing a multiplicity of aligned groups of sources of visible light; means to move said shaped article relative to said groups of light sources while maintaining the line of movement of said article aligned with said light source alignment; means o vary the luminous flux density of visible light such that different flux densities of visible light are emitted from said groups of light sources; means to continuously irradiate said article with sufficient visible light, to an extent of about 100 to 1,000,000 luxes, to cure and harden said article; sensing means to detect the temperature proximate to said shaped article; means to control the temperature of said shaped article responsive to said sensing means during said visible light curing thereof independent of said radiation and independent of said curing to a predetermined temperature; and means for recovering a cured, hardened shaped article.

11. An apparatus as claimed in claim 10 wherein at least one of said groups of sources of light comprises one source.

12. An apparatus as claimed in claim 10 wherein said means to control said temperature is a heating means.

13. An apparatus as claimed in claim 10 wherein said means to control said temperature is a cooling means.

14. An apparatus as claimed in claim 10 including means to light cure a multiplicity of said articles in a continuous manner.

15. An apparatus as claimed in claim 10 wherein said light source groups are linearly aligned.

16. An apparatus as claimed in claim 14 including means to move said multiplicity of articles relative to spatially fixed light source groups.

17. An apparatus as claimed in claim 10 including means to vary said luminous flux densities in a step-wise manner.

18. An apparatus as claimed in claim 10 wherein there is a relationship between the depth of hardening within said article as a function of the time of said curing, and including means to vary said luminous flux density emitted from said visible light source groups such as to cause said hardening to a related depth at a specified time.

* * * * *